United States Defensive Publication [19] (H) [11] T105,001

Parton et al. [43] Jan. 1, 1985

[54] ADSORBABLE ALKYNYL SUBSTITUTED HETEROCYCLIC QUATERNARY AMMONIUM SALTS AND APPLICATIONS THEREOF TO SILVER HALIDE PHOTOGRAPHY

[76] Inventors: Richard L. Parton; Wilbur S. Gaugh; Karl E. Wiegers, all of Kodak Park Div., Rochester, N.Y. 14650

[21] Appl. No.: 584,280

[22] Filed: Feb. 27, 1984

Related U.S. Application Data

[62] Division of Ser. No. 503,470, Jun. 13, 1983.

[51] Int. Cl.[3] ..... G03C 5/54; G03C 1/485; C07D 233/54; C07D 215/38

[52] U.S. Cl. ..... 430/217; 430/598; 546/159; 546/171; 546/331; 548/162; 548/163; 548/251; 548/341; 548/557; 548/567

[57] ABSTRACT

The use of thioamido and alkynyl substituted heterocyclic ammonium salts in producing images in silver halide photographic elements is disclosed. The thioamido and alkynyl substituted heterocyclic ammonium salts can be incorporated in photographic silver halide emulsions. The thioamido substituent is capable of promoting adsorption of these salts to silver halide grain surfaces. In negative working surface latent image forming emulsions the thioamido and alkynyl substituted heterocyclic ammonium salts permit higher speeds to be achieved. In direct positive internal latent image forming emulsions nucleation activity and improved incubation stability can be achieved.

1 Claim, No Sheets Drawing,

82 Pages Specification

The file of this unexamined application may be inspected and copies thereof may be purchased (849 O.G. 1221, Apr. 9, 1968).